(12) United States Patent
Dell'Oca (10) Patent No.: US 9,788,875 B2
(45) Date of Patent: *Oct. 17, 2017

(54) CRIMP WITH AN INSERT TO HOLD A CABLE

(75) Inventor: Alberto A. Fernandez Dell'Oca, Montevideo (UY)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 143 days.

This patent is subject to a terminal disclaimer.

(21) Appl. No.: 13/002,621

(22) PCT Filed: Nov. 5, 2008

(86) PCT No.: PCT/US2008/082462
§ 371 (c)(1),
(2), (4) Date: Jan. 4, 2011

(87) PCT Pub. No.: WO2010/014119
PCT Pub. Date: Feb. 4, 2010

(65) Prior Publication Data
US 2011/0224676 A1 Sep. 15, 2011

Related U.S. Application Data

(60) Provisional application No. 61/084,289, filed on Jul. 29, 2008.

(51) Int. Cl.
*A61B 17/58* (2006.01)
*A61B 17/60* (2006.01)
(Continued)

(52) U.S. Cl.
CPC .................. *A61B 17/82* (2013.01)

(58) Field of Classification Search
CPC ...... A61B 17/82; A61B 17/823; A61B 17/826; A61B 17/8869; A61B 17/8861;
(Continued)

(56) References Cited

U.S. PATENT DOCUMENTS 3,879,147 A * 4/1975 Morell .......................... 403/369
3,938,902 A * 2/1976 Morell ....................... E04C 5/12
174/84 S (Continued)

FOREIGN PATENT DOCUMENTS

| DE | 196 28 147 | 1/1998 |
|---|---|---|
| EP | 0596277 | 5/1994 |
| EP | 0625336 | 11/1994 |

*Primary Examiner* — Eduardo C Robert
*Assistant Examiner* — Michelle C Eckman
(74) *Attorney, Agent, or Firm* — Fay Kaplun & Marcin, LLP (57) ABSTRACT

An apparatus for securing a cerclage member about a bone within a living body comprises a crimp including a first space extending longitudinally therethrough from a first space proximal opening to a first space distal opening, the first space sized and shaped to slidably receive a cerclage member therein and a second space extending parallel to the first space from a second space proximal opening to a second space distal opening, the second space including a proximal portion to receive the cerclage member and a distal portion decreasing in cross-sectional area and an insert that, when inserted into the second space distal opening adjacent to a cerclage member, a decreasing cross-sectional area of the second space distal portion forces the insert laterally relative to a longitudinal axis of the second space, pinching and locking the cerclage member against movement relative to the crimp.

16 Claims, 6 Drawing Sheets

(51) Int. Cl.
*A61F 2/00* (2006.01)
*A61B 17/82* (2006.01)

(58) Field of Classification Search
CPC .............. A61B 17/842; A61B 17/7053; Y10T 24/3969; Y10T 24/3996; F16G 11/00; F16G 11/02; F16G 11/04; F16G 11/05
USPC .......................... 606/74, 103, 263, 277, 324
See application file for complete search history.

(56) References Cited

U.S. PATENT DOCUMENTS

| | | | | |
|---|---|---|---|---|
| 3,952,377 | A * | 4/1976 | Morell | 24/136 R |
| 4,156,574 | A * | 5/1979 | Boden | 403/211 |
| 4,730,087 | A * | 3/1988 | Werner | H01R 4/5033 |
| | | | | 174/94 R |
| 5,090,923 | A * | 2/1992 | Kenyon | H01R 4/08 |
| | | | | 174/94 R |
| 5,356,417 | A * | 10/1994 | Golds | 606/151 |
| 5,435,044 | A * | 7/1995 | Ida | 24/136 R |
| 5,908,421 | A * | 6/1999 | Beger | A61B 17/82 |
| | | | | 606/151 |
| 6,099,527 | A * | 8/2000 | Hochschuler et al. | 606/279 |
| 6,277,120 | B1 * | 8/2001 | Lawson | 606/263 |
| 6,589,246 | B1 * | 7/2003 | Hack et al. | 606/74 |
| 6,684,585 | B2 * | 2/2004 | Campbell | E04C 5/08 |
| | | | | 403/2 |
| 7,250,054 | B2 * | 7/2007 | Allen et al. | 606/74 |
| 7,846,181 | B2 * | 12/2010 | Schwartz et al. | 606/232 |
| 2008/0208205 | A1 * | 8/2008 | Kraemer | A61B 17/82 |
| | | | | 606/103 |
| 2009/0171357 | A1 * | 7/2009 | Justin et al. | 606/60 |
| 2009/0248028 | A1 * | 10/2009 | Alexander | 606/103 |
| 2009/0292317 | A1 * | 11/2009 | Belliard | 606/263 |
| 2012/0130373 | A1 * | 5/2012 | Larroque-Lahitette | 606/74 |
| 2012/0215224 | A1 * | 8/2012 | Songer | 606/74 |

* cited by examiner

CRIMP WITH AN INSERT TO HOLD A CABLE

PRIORITY CLAIM

The present application is a National Phase application of PCT Patent Application Serial No. PCT/US2008/082462 filed on Nov. 5, 2008 which claims priority to U.S. Provisional Patent Application Ser. No. 61/084,289 filed on Jul. 29, 2008 entitled "Clamp with an Insert to Hold Cable and Method." The entire disclosure of this application is expressly incorporated herein by reference.

FIELD OF THE INVENTION

The invention relates generally to surgical methods and apparatus for treating bones and more particularly relates to a method and apparatus for bone fixation using cable for a bone cerclage technique.

BACKGROUND INFORMATION

The treatment of bones often involves a bone cerclage technique wherein a wire or other cable is used to aid bone fixation or repair. Bone cerclage procedures generally require that a wire or cable be looped around the bone and secured tightly. Present bone cerclage devices and methods require at least one incision adjacent the target portion of bone large enough to permit the insertion of bone cerclage tools used to insert and secure the cable around the bone.

SUMMARY OF THE INVENTION

The present invention is directed to an apparatus for securing a cerclage member about a bone within a living body comprising a crimp including a first space extending longitudinally therethrough from a first space proximal opening to a first space distal opening, the first space sized and shaped to slidably receive a cerclage member therein and a second space extending substantially parallel to the first space from a second space proximal opening to a second space distal opening, the second space including a proximal portion sized and shaped to slidably receive the cerclage member therein and a distal portion decreasing in cross-sectional area from the second space distal opening to the proximal portion and an insert sized and shaped so that, when inserted into the second space distal opening adjacent to a cerclage member inserted therethrough, the decreasing cross-sectional area of the second space distal portion forces the insert laterally relative to a longitudinal axis of the second space pinching the cerclage member and locking the cerclage member against movement relative to the crimp.

DETAILED DESCRIPTION

The present invention may be further understood with reference to the following description and the appended drawings, wherein like elements are referred to with the same reference numerals. The present invention relates generally to methods and devices for the stabilization and fixation of fractured bones and bone fragments via bone cerclage. Specifically, the present invention relates to methods and devices for securing a cerclage wire or cable in a desired position looped around a target portion of bone. Embodiments of the present invention may also be employed with any of a plurality of bone treatment procedures requiring a bone cerclage. As used in this application, the terms proximal and distal refer to direction along the cerclage cable with a first end of the cable being identified as the proximal end and a second end of the cable being identified as distal. Components of the crimp will then be described in relation to the direction in which the cable passes therethrough. For example, an opening to a lumen into which a distal end of the cable is inserted and against which a proximal end of the cable is held will be described as the proximal opening of the lumen. The opposite end of the lumen from which the distal end of the cable exits will be described as the distal opening of the lumen and the other elements of the crimp will be similarly identified.

As shown in FIGS. 1-4, a crimping device 100 according to a first exemplary embodiment of the invention comprises a crimp 102 for receiving a cable 10 to be looped around a target portion of a bone (not shown). The crimp 102 comprises a cable lumen 108 and a crimp lumen 118 extending substantially parallel to one another along a longitudinal length of the crimp 102. As described in more detail below, the distal end of a cable 10 is inserted into the cable lumen 108 via a proximal opening 114 thereof until an enlarged proximal end 12 thereof engages the portion of the crimp 102 surrounding the opening 114 preventing the cable 10 from being drawn further into the lumen 108. The distal end of the cable 10 is then drawn from a distal opening 112 of the lumen 108 and looped around the bone to return to the crimp 102. The distal end of the cable 10 is then inserted into the crimp lumen 118 via a proximal opening 124 until it passes out of the crimp lumen 118 via a distal opening 122 on the opposite side of the crimp 102. An insert 126 is then placed over the distal end of the cable 10 and slid along the cable 10 until it enters the distal opening 122. As described in more detail below, the crimp lumen 118 is tapered with a diameter thereof decreasing from a maximum at the distal opening 122 to a minimum proximally thereof. After the cable 10 has been tensioned to a desired level, the insert 126 is forced proximally into the tapered distal portion of the crimp lumen 118 so that the inward taper of the distal portion of the crimp lumen 118 exerts radially inwardly directed force against the insert 126 which increases as the insert is forced further into the crimp lumen 118. This force crushes the insert 126 against the cable 10 locking it in place over the cable 10 and preventing the cable 10 from moving proximally out of the opening 124. This locks the cable 10 in the desired position around the bone and maintains the desired tension on the cable 10. A proximal portion of the insert 126 may, for example, be sized and shaped to frictionally engage the tapered portion of the crimp lumen 118. However, those skilled in the art will understand that the tension of the cable 10 will draw the insert 126 further into the crimp lumen 118 securing it therein.

Figure 1:
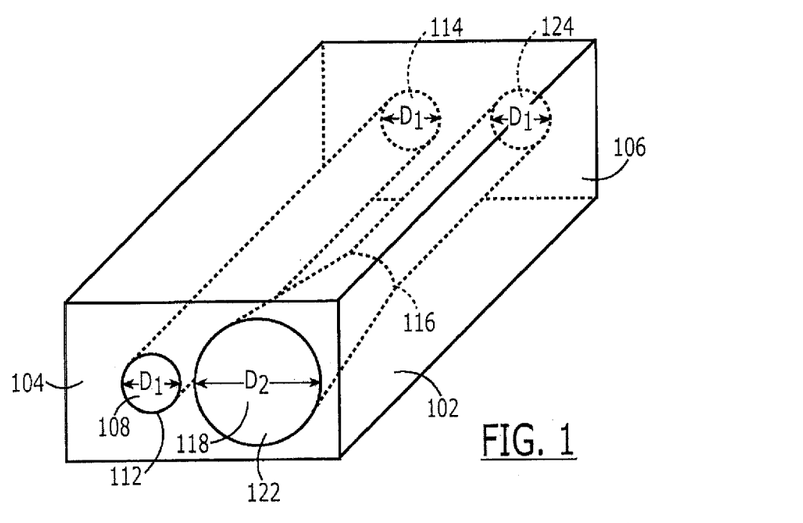
FIG. 1 shows a perspective view of a crimp according to a first embodiment of the invention.
Figure 2:
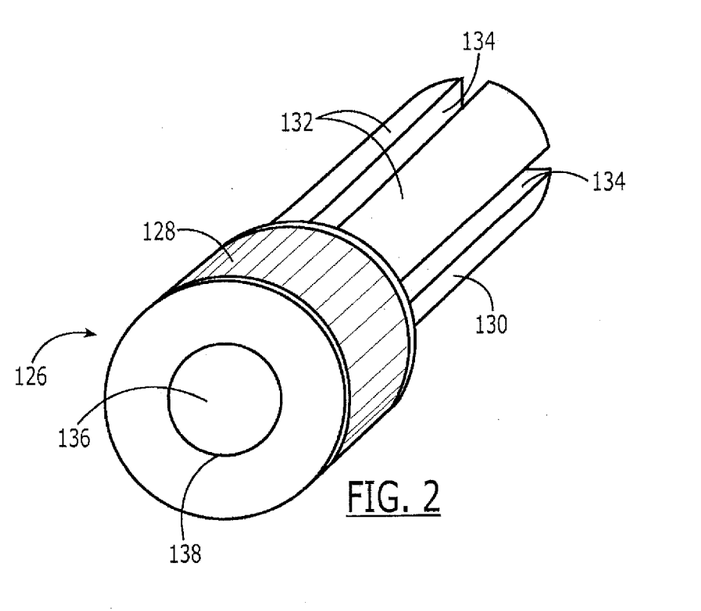
FIG. 2 shows a perspective view of an insert to be used with the crimp of FIG. 1.

The crimp 102 may be formed of any suitable biocompatible material as would be understood by those skilled in the art so long as this material exhibits rigidity sufficient to withstand the forces applied thereto when deployed in the body. Exemplary materials for the crimp 102 and insert 126 include, but are not limited to, stainless steel, titanium, titanium alloys, Polyetheretherketone ("PEEK") or any combination thereof. As would be understood by those skilled in the art, the cable lumen 108 is formed with a size and shape permitting the selective insertion of the cable 10 therethrough with, for example, a substantially uniform diameter $D_1$ slightly greater than an outer diameter of the cable 10. In an exemplary embodiment, the lumen 108 is substantially circular. It is noted, that the cross-section of the cable lumen 108 may comprise any shape suited to a shape of the cable 10. The crimp lumen 118 extends longitudinally from a proximal end 122 to a distal end 124 and is separated from the cable lumen 108 along a distal face 104 of the crimp 102 by a desired distance which may, for example, be selected to minimize the size of the crimp 102 while maintaining the structural integrity thereof. The crimp lumen 118 may for example, be substantially circular in cross-section, tapering from a diameter $D_2$ at the distal opening 122 to a diameter $D_1$ at a taper end point 116 located at any desired point within the crimp lumen 118. In one embodiment, the taper end point 116 is located midway between the distal opening 122 and the proximal opening 124. Alternatively, the taper end point 116 may be located at any point enabling the insert 126 to be suitable crushed against the cable 10, as will be described in greater detail hereinafter. The remainder of the crimp lumen 118 located distally of the taper end point 116 may comprise a uniform diameter $D_1$. Furthermore, those skilled in the art will understand that the diameter $D_1$ of the crimp lumen 118 may be substantially equal to the diameter $D_1$ of the cable lumen 108 as it will accommodate the same cable 10. However, this is not necessary and the diameter $D_1$ may be any value sufficient to receive the cable 10 and small enough to prevent the passage of the insert 126 proximally therethrough.

The insert 126 according to the first embodiment of the present invention is formed as an elongated nail extending from an increased diameter head 128 at a distal end thereof to a slotted shaft 130 at a proximal end. Specifically, a plurality of arms 132 spaced from one another circumferentially by a plurality of slots 134 extending proximally from the head 128 in a substantially cylindrical configuration defining a lumen 136 which extends through the insert 126 from a distal opening 138 to a proximal opening 140. The lumen 136 is sized and shaped to slidably receive the cable 10 therethrough and, in an exemplary embodiment, has a diameter $D_1$ sufficient to slidably receive the cable 10 therethrough. A diameter of the head 128 may be made greater than a diameter $D_2$ of the proximal end 122 of the crimp lumen 118 to prevent insertion of the insert 126 thereinto beyond a predetermined distance. However, this is not necessary as the tapered portion of the crimp lumen 118 and the proximal portion of the crimp lumen 118 will be selected to prevent the passage of the insert 126 therethrough.

Figure 3:
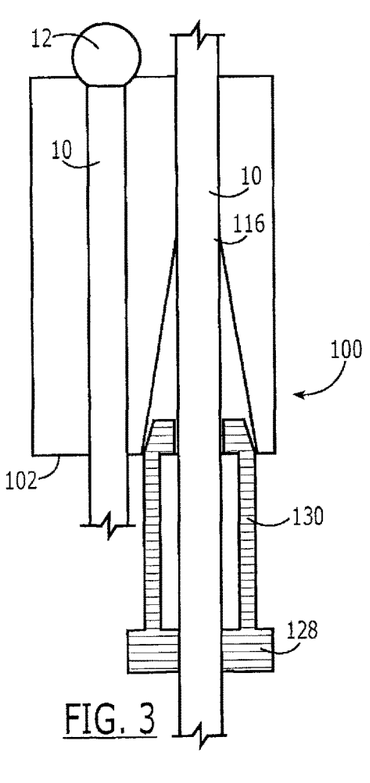
FIG. 3 shows a partial cross-sectional view of the crimp of FIG. 1 in an unlocked configuration.
Figure 4:
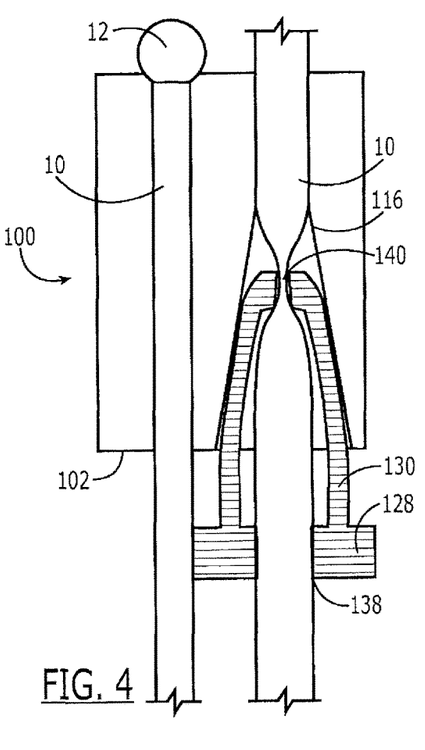
FIG. 4 shows a partial cross-sectional view of the crimp of FIG. 1 in a locked configuration.

FIGS. 3-4 sequentially depict the process by which the cable 10 is locked onto the crimp 102 in accordance with a first exemplary method of the present invention. Initially, the distal end of the cable 10 is inserted into the cable lumen 108 via the distal opening 114 until the enlarged proximal end 12 of the cable 10 prevents the cable 10 from being further inserted thereinto. Engagement of the enlarged proximal end 12 with the distal face 106 locks the distal end of the cable 10 against the crimp 102. The cable 10 is then drawn out of the cable lumen 108 via the distal opening 112 and looped around the bone in a desired position. After being looped around the bone, the distal end of the cable 10 is inserted into the crimp lumen 118 via the proximal opening 124 and passed therethrough to exit via the distal opening 122. The distal end of the cable 10 is then inserted into the lumen 136 of the insert via the distal opening 138 and the insert 126 is slid proximally over the cable 10. Tension may then be applied to the cable 10 until a desired level of tension is obtained and the insert 126 is slid proximally over the cable 10 until a proximal end of the insert 126 enters the distal opening 122 of the crimp lumen 118, as shown in FIG. 3. It is noted that, in the position shown in FIG. 3, radially constrictive pressure has not yet been applied to the arms 132 which are not yet deflected radially inward. Alternatively, the insert 126 may be assembled within the distal opening 122 of the crimp lumen 118 in the position of FIG. 3 in the factory so that a user may thread the cable 10 through the crimp lumen 118 and the lumen 136 of the insert 126 in a single step. For example, the insert 126 may be held in this position through a friction fit between the proximal end of the insert 126 and the distal end of the crimp lumen 118. As the proximal end of the insert 126 is not yet pinched radially inward in this configuration, the cable 10 passes easily through the lumen 136. The insert 126 may then be driven the desired distance into the crimp lumen 118 during the tensioning process. That is, the tensioning mechanism (not shown) may be abutted against the distal head 128 of the insert 126 so that, as tension on the cable 10 is increased, the tensioning mechanism applies increasing proximally directed force against the insert 126 forcing the insert 126 into the crimp lumen 118 to force the arms 130 radially inward into the lumen 136 pinching the cable 10 and locking the cable 10 in the desired position at the desired tension, as shown in FIG. 4. As would be understood by those skilled in the art, this radially inward force may deform pinched portion of the cable 10 further aiding in locking the cable 10 in the desired position within the crimp 102.

Figure 5:
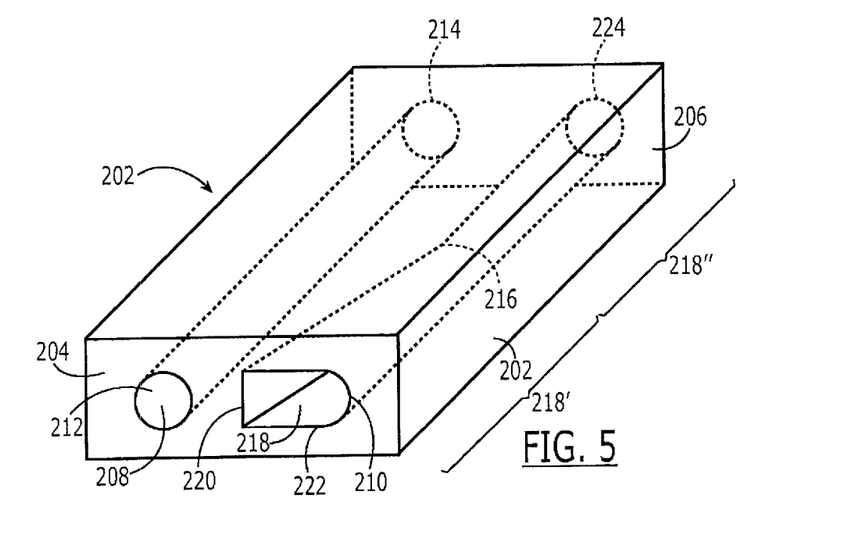
FIG. 5 shows a perspective view of a crimp according to a second embodiment of the invention.
Figures 6, 7:
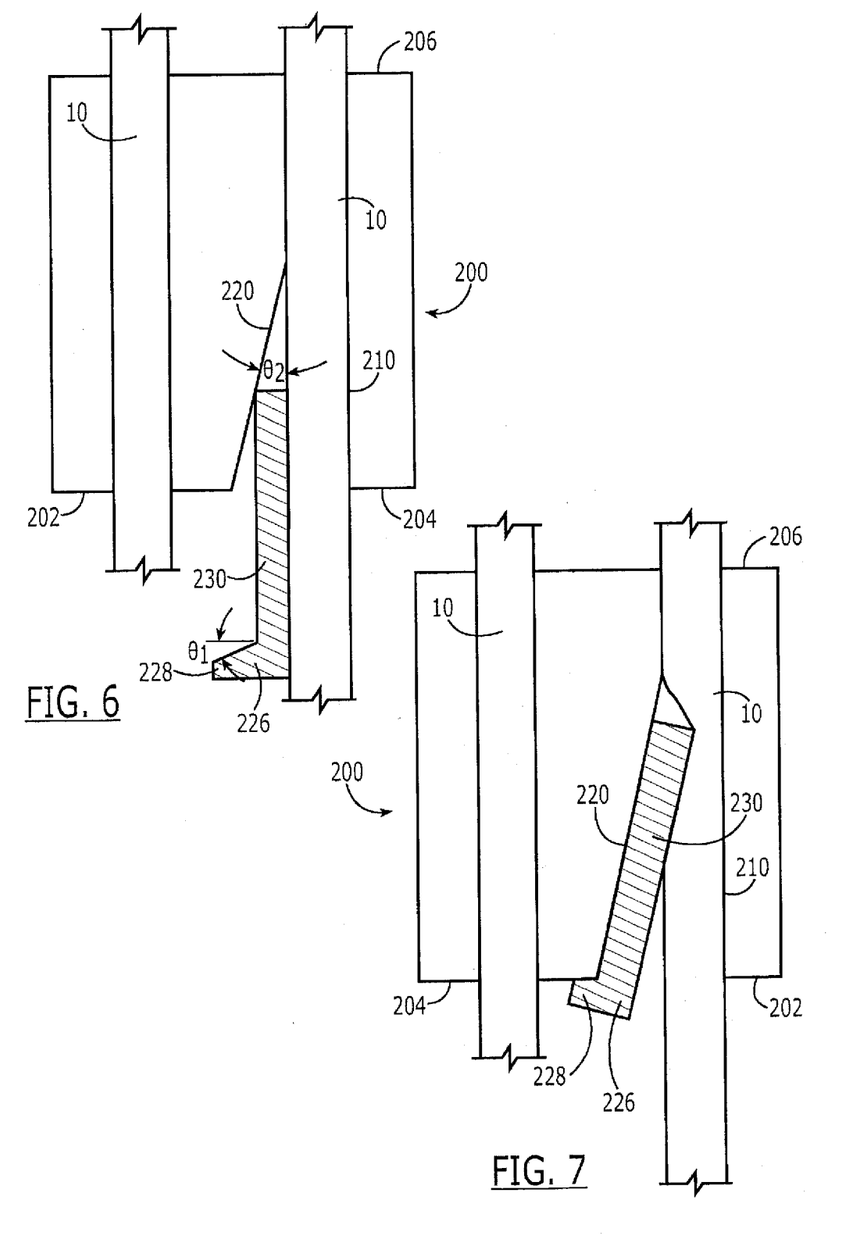
FIG. 6 shows a partial cross-sectional view of the crimp of FIG. 5 in an unlocked configuration.
FIG. 7 shows a partial cross-sectional view of the crimp of FIG. 5 in a locked configuration.
Figure 8:
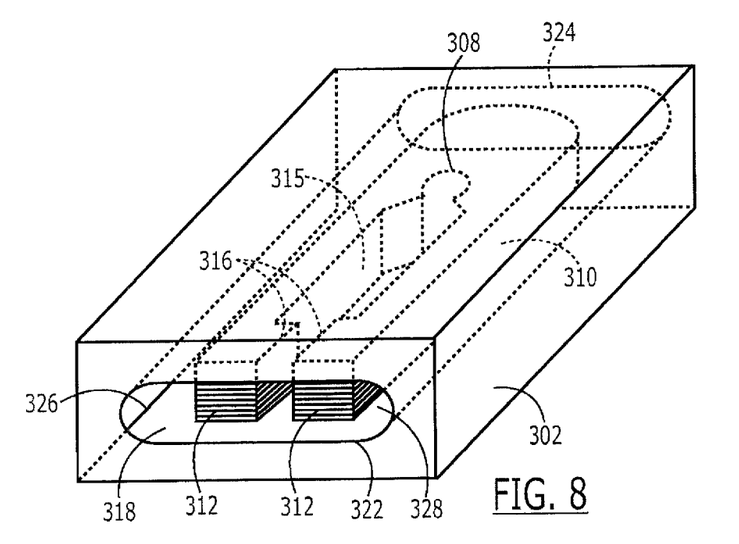
FIG. 8 shows a perspective view of a crimp according to a third embodiment of the invention.
Figure 9:
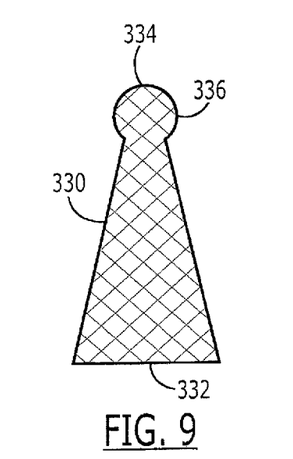
FIG. 9 shows a perspective view of an insert to be used with the crimp of FIG. 8.

The crimp lumen 118 may be formed in any desired size and shape as would be understood by those skilled in the art. As shown in FIGS. 5-7, a crimp 202 according to a further embodiment of the invention includes a distal end 222 of a crimp lumen 218 having a substantially D-shaped cross section. Specifically, a cross section of the distal portion of the crimp lumen 218 comprises a substantially planar wall 220 connected to an arched portion 210. A distal portion 218' of the crimp lumen 218 tapers down in size from a maximum at the distal opening 222 to a taper end point 216. A distal portion 218" of the crimp lumen 218 located proximally of the taper end point 216 has a substantially circular cross section similar to the crimp lumen 118 of FIGS. 1-4. A cable lumen 208 extends longitudinally through the crimp 202, substantially parallel to the crimp lumen 218. As described earlier with respect to FIGS. 1-4, a diameter $D_1$ of the cable lumen 208 and the proximal portion 218" of the crimp lumen 218 may be substantially equivalent to an outer diameter of the cable 10.

As would be understood by those skilled in the art, an exemplary insert 226 for use with the crimp 202 is sized and shaped to be inserted into the distal portion 218' of the crimp lumen 218 and to be forced by the tapered shape thereof to apply a radially inward locking pressure against the cable 10 when driven into the distal portion 218' of the crimp lumen 218. The insert 226 is formed as a nail including an increased diameter head 228 extending radially outward from a distal end thereof and an elongated shaft 230 extending proximally from the head 228. The shaft 230 may be formed as a substantially rectangular element with a thickness selected to reside easily beside the cable 10 within the distal opening 222 but which, when driven proximally into the tapered distal portion 218', will be compressed against the cable 10 applying an increasing lateral force thereto until a desired locking position of the insert 226 is reached. Specifically, the head 228 projects laterally from the insert 226 on a side thereof which faces away from the cable 10 (i.e., away from the arched side of the opening 222). A proximal surface of the head 228 is tapered at an angle $\theta_1$ substantially equivalent to a taper angle $\theta_2$ of the wall 220 so that, when the insert 226 is fully inserted into the crimp lumen 218 and a surface of the shaft 230 has been pushed against the tapered surface of the crimp lumen 218, the tapered proximal surface of the head 228 lies substantially flush against a distal face 204 of the crimp 202, as those skilled in the art will understand. Furthermore, engagement of the head 228 with the proximal face 204 prevents insertion of the insert 226 into the crimp lumen 218 beyond a desired predetermined distance. When in this position, as can be seen in FIG. 7, the proximal end of the shaft 230 has pinched the cable 10 and compressed an adjacent surface thereof locking the cable 10 in the desired position and maintaining the desired tension thereon.

FIGS. 6-7 sequentially depict the process by which the cable 10 is locked onto the crimp 202. In a manner similar to that described above for the crimp 102, a distal end of the cable 10 is inserted into the cable lumen 208 via the proximal opening 214 until the enlarged proximal end 12 engages a proximal face 206 of the crimp 202. At this point, the distal end of the cable 10 has passed out of the cable lumen 208 via the distal opening 212. The cable 10 is then looped around the bone in a target position and the distal end of the cable is inserted into the crimp lumen 218 via the proximal opening 224. The cable 10 is passed through the crimp lumen 218 to exit therefrom via the distal opening 222. The distal end of the cable 10 is then coupled to any known tensioning mechanism (not shown) as would be understood by those skilled in the art and the insert 226 is inserted into the distal opening 222 adjacent to the cable 10 as shown in FIG. 6. The tensioning mechanism may then be actuated to increase the tension on the cable 10 until a desired level has been reached. As described above in regard to the crimp 102, the tensioning mechanism may be abutted against the insert 226 so that, as the cable 10 is tensioned to the desired level, the tensioning mechanism may force the insert 226 into the crimp lumen 218 until the cable 10 has been locked in position at the desired tension as shown in FIG. 7.

Figure 10:
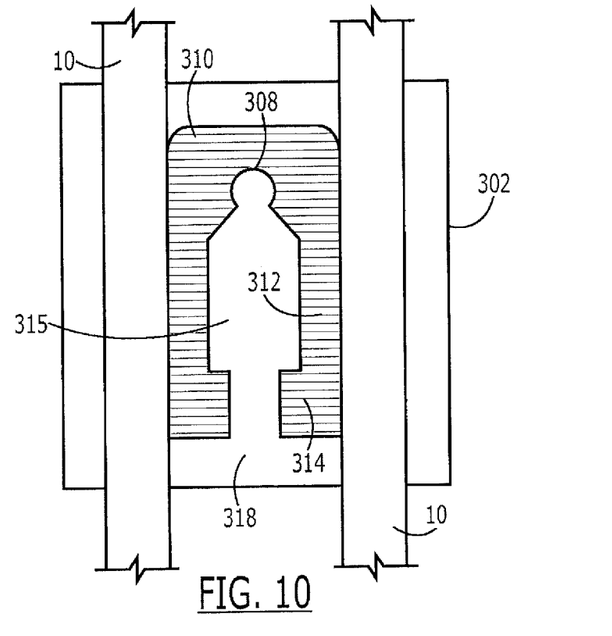
FIG. 10 shows a partial cross-sectional view of the crimp of FIG. 8 in an unlocked configuration.
Figure 11:
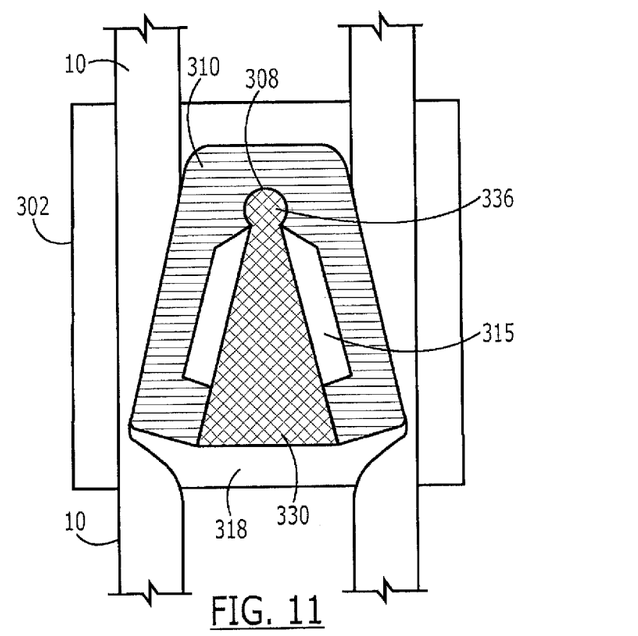
FIG. 11 shows a partial cross-sectional view of the crimp of FIG. 8 in a locked configuration.

As shown in FIGS. 8-11, a crimp 302 according to another embodiment of the invention, includes a single lumen 318 extending longitudinally therethrough from a proximal end 324 to a proximal end 324. The lumen 318 is formed with a oblong cross-section and maintains a substantially uniform cross-sectional area. An insert 310 received within the lumen 318 includes sides which, in an initial configuration, are spaced from each of the lateral edges of the lumen 318 by spaces 326 and 328 sized to permit the cable 10 to pass through the lumen 318 on either side of the insert 310 as shown in FIG. 10. As would be understood by those skilled in the art, at least one of the proximal and distal openings 324, 322, respectively, of the lumen 318 may be made slightly smaller than a cross-sectional area of the insert 310 to prevent the insert 310 from passing therethrough. The insert 310 is substantially U-shaped with a longitudinal length less than that of the crimp 302. Specifically, the insert 310 comprises a pair of substantially parallel arms 312 extending distally from a proximal joint 314 and separated from one another by a space 315. A distal end 316 of each of the arms 312 is expanded to project into the space 315 forming a narrow entrance to the space 315 at the distal end thereof. A proximal end of the space 1315 forms a groove 308 which as described in more detail below, is sized and shaped to receive the proximal end of a wedge member 330 which is inserted into the space 315 to lock the cable within the crimp 302.

The wedge member 330 is substantially triangular with a proximal end formed as a plug 334 which may, for example, be substantially cylindrical, which is sized and shaped to be received in the groove 308. The plug 334 is also sized so that it may be slid between the distal ends 316 of the arms 312 to force the arms from the initial configuration shown in FIGS. 8 and 10 to the locking configuration shown in FIG. 11. Specifically, after the cable 10 has been passed through the space 326 of the lumen 318, looped around the bone and passed through the space 328 on the opposite side of the lumen 318 and tensioned as desired as will be described in more detail below, the wedge member 330 is driven into the insert 310 with the plug 334 sliding between the distal ends 316 of the arms 312, the tapered sides of the wedge member 330 force the arms 312 further from each other so that lateral sides thereof are forced into the spaces 326 and 328 driving the cable 10 against the walls of the lumen 318 and locking the cable 310 in position while maintaining the desired tension thereon. That is, as the width of the wedge member 330 increases from the proximal end to the distal end, the further proximally the wedge is driven into the space 315, the further the distal ends 316 of the arms 312 are driven laterally from one another urging the laterally outer sides of the aims 312 into contact with the cable 10 locking both the proximal and distal portions thereof against the walls of the lumen 318 in the spaces 326 and 328.

In use, a distal end of a cable 10 which in this embodiment may or may not include an enlarged proximal end, is inserted into the space 326 of the lumen 318 via the proximal opening 324 to exit the crimp 302 via the distal opening 322. The cable 10 is then looped around the bone along a desired path and reinserted into the crimp 302 via the opening 324. This time the distal end of the cable is passed through the space 328 to exit the distal opening 322 and connected to a tensioning mechanism. When the desired tension has been applied to the cable 10, the wedge member 330 is driven into the space 315 by applying a proximally directed force to a distal end 332 thereof until the plug 334 is seated in the groove 308 locking the cable 10 to the crimp 302 in the desired position and with the desired tension.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. An apparatus for securing a cerclage member about a bone within a living body, the apparatus comprising:
a crimp including a first space extending longitudinally therethrough from a first space proximal opening to a first space distal opening, the first space sized and shaped to slidably receive a cerclage member therein and a second space extending substantially parallel to the first space from a second space proximal opening to a second space distal opening, the second space including a cylindrical proximal portion sized to slidably receive the cerclage member therein and a distal portion, a tapering of the distal portion decreasing in cross-sectional area from the second space distal opening and terminating at a distal end of the proximal portion at a location along the second space that is distal of the second space proximal opening; and
an insert sized and shaped so that, when inserted into the second space distal opening adjacent to a cerclage member inserted therethrough, the decreasing cross-sectional area of the second space distal portion forces the insert laterally relative to a longitudinal axis of the second space pinching the cerclage member at a pinching point decreasing a cross-sectional size of the cerclage member at the pinching point and locking the cerclage member against movement relative to the crimp.

2. The apparatus of claim 1, wherein the distal portion of the second space tapers from a maximum width at the second space distal opening to a minimum width at a taper end point between the proximal and distal portions of the second space.

3. The apparatus of claim 2, wherein the insert includes a lumen sized and shaped to slidably receive the cerclage member therein, the lumen being collapsed as the insert is forced into the second space distal opening to pinch the cerclage member within the lumen of the insert.

4. The apparatus of claim 3, the insert comprising a plurality of arms projecting proximally therefrom surrounding the lumen of the insert, the arms being separated from one another circumferentially by a plurality of slots extending longitudinally through the insert.

5. The apparatus of claim 3, wherein a cross section of the insert is substantially circular.

6. The apparatus of claim 3, wherein a cross section of the distal portion of the second space is non-circular.

7. The apparatus of claim 6, wherein the distal portion of the second space is substantially D-shaped with a first rounded side shaped to correspond to a shape of the cerclage member and a second side opposite the first side shaped to slidably receive the insert.

8. The apparatus of claim 7, wherein the first side of the distal portion of the second space is substantially parallel to the longitudinal axis of the second space while the second side of the distal portion of the second space intersects the longitudinal axis of the second space at a predetermined taper angle.

9. The apparatus of claim 8, wherein the insert further comprises a head projecting laterally from a distal end of the insert.

10. The apparatus of claim 9, wherein a proximal face of the head of the insert is formed in a plane intersecting a plane perpendicular to the longitudinal axis of the second space at an angle substantially equal to the taper angle.

11. The apparatus of claim 2, wherein the insert is formed as a shaft shaped to be inserted on one side of the cerclage member to pinch the cerclage member between a proximal end of the insert and a wall of the second space as the insert is forced into the second space distal opening.

12. The apparatus of claim 2, wherein a cross section of the distal portion of the second space is substantially circular.

13. The apparatus of claim 1, wherein the first space and the second space are formed as separate lumens separated from one another by a wall.

14. An apparatus for securing a cerclage member about a bone within a living body, the apparatus comprising:
a crimp including a lumen extending longitudinally therethrough from a proximal opening to a distal opening; and
an insert received within the lumen, the insert being sized and shaped so that, when in an initial configuration, lateral sides thereof extend substantially parallel to walls of the lumen forming a first space on a first side of the insert sized to slidably receive therein a cerclage member to be bound around a target portion of bone and forming, on a second side of the lumen a second space sized to slidably receive the cerclage member, the insert including a void between the first and second sides thereof and an opening to the void at a distal end of the insert; and
a wedge member including a reduced width proximal end and sized to be received within the opening at the distal end of the insert, a width of the wedge member tapering from the reduced width proximal end to a maximum width distally therefrom, the wedge member being sized so that, when driven into the void via the opening at the distal end of the insert, the taper of the wedge member drives the first and second sides of the insert laterally outward into the first and second spaces to secure the cerclage member therein, wherein the insert includes a groove at a proximal end of the void and extending along a longitudinal axis of the insert, the wedge member including a plug at a proximal end thereof that is received in the groove when the wedge member is inserted into the void in a desired configuration in response to a longitudinally directed force.

15. The apparatus of claim 14, wherein the insert is substantially U-shaped with the first and second arms connected to one another via a joint at a proximal end thereof.

16. The apparatus of claim 14, wherein distal ends of the first and second arms of the insert include projections extending laterally inward toward one another and separated from one another by a width less than a width of the void.

* * * * *